United States Patent
Yang et al.

(10) Patent No.: US 10,458,951 B2
(45) Date of Patent: Oct. 29, 2019

(54) CYLINDER BLOCK INSPECTION METHOD AND SYSTEM

(71) Applicant: GM Global Technology Operations LLC, Detroit, MI (US)

(72) Inventors: Jianghuai Yang, Rochester Hills, MI (US); Martin S. Kramer, Clarkston, MI (US); Qigui Wang, Rochester Hills, MI (US); Yucong Wang, West Bloomfield, MI (US); Zhe Li, Rochester, MI (US)

(73) Assignee: GM GLOBAL TECHNOLOGY OPERATIONS LLC, Detroit, MI (US)

( * ) Notice: Subject to any disclaimer, the term of this patent is extended or adjusted under 35 U.S.C. 154(b) by 284 days.

(21) Appl. No.: 15/145,418

(22) Filed: May 3, 2016

(65) Prior Publication Data

US 2017/0322183 A1 Nov. 9, 2017

(51) Int. Cl.
| | |
|---|---|
| *C23C 4/18* | (2006.01) |
| *F02F 1/18* | (2006.01) |
| *G01N 29/14* | (2006.01) |
| *G01N 29/04* | (2006.01) |
| *C23C 4/00* | (2016.01) |
| *F02F 1/00* | (2006.01) |

(52) U.S. Cl.
CPC .............. *G01N 29/04* (2013.01); *C23C 4/18* (2013.01); *F02F 1/18* (2013.01); *G01N 29/14* (2013.01); *C23C 4/00* (2013.01); *F02F 2001/008* (2013.01); *G01N 2291/0289* (2013.01); *G01N 2291/101* (2013.01); *G01N 2291/106* (2013.01); *G01N 2291/2636* (2013.01)

(58) Field of Classification Search
CPC .......... G01N 29/04; G01N 2291/2636; G01N 2291/101; F02F 1/18; F02F 2001/008; C23C 4/00
USPC .......................................................... 73/587
See application file for complete search history.

(56) References Cited

U.S. PATENT DOCUMENTS

| | | | | |
|---|---|---|---|---|
| 4,444,049 A | * | 4/1984 | Hitchcock | F02B 77/08 73/114.28 |
| 5,271,967 A | * | 12/1993 | Kramer et al. | C23C 4/12 73/587 |
| 2005/0159912 A1 | * | 7/2005 | Ruzzo | G01N 27/90 702/108 |
| 2007/0180898 A1 | * | 8/2007 | Nagel | F02M 65/00 73/114.77 |
| 2008/0060415 A1 | * | 3/2008 | Butler | G01M 3/3272 73/37 |
| 2009/0014438 A1 | * | 1/2009 | Ohashi | H05B 6/062 219/627 |
| 2016/0138502 A1 | * | 5/2016 | Bullister et al. | G07C 5/00 73/119 |

FOREIGN PATENT DOCUMENTS

JP 2007139653 * 7/2007

* cited by examiner

*Primary Examiner* — Jacques M Saint Surin

(57) ABSTRACT

A system for inspecting thermal spray coated cylinder bores of aluminum alloy cylinder blocks, the system includes a failure detection apparatus, a heating apparatus, a cooling apparatus, and a control unit in electronic communication with each of the failure detection apparatus, the heating apparatus, and the cooling apparatus, and wherein the control unit includes a memory and a control logic sequence for operating the system.

19 Claims, 3 Drawing Sheets

CYLINDER BLOCK INSPECTION METHOD AND SYSTEM

TECHNICAL FIELD

The present disclosure relates to metal casting and more specifically to aluminum cylinder block castings having thermal spray bores and methods of manufacture.

BACKGROUND

The statements in this section merely provide background information related to the present disclosure and may or may not constitute prior art.

A typical cast aluminum cylinder block includes a number of cylinders arranged in a number of configurations. The improvement achieved by using aluminum alloys for casting cylinder blocks includes a higher strength to weight ratio compared with grey iron or other ferrous based casting. However, whereas the cylinder bores of grey iron castings can simply be machined and honed before assembly, most aluminum alloy blocks utilize some type of cylinder bore liner. Some examples of cylinder bore liners include cast-in or press-in place iron or steel liners. Recent developments in cylinder bore liners include techniques known as thermal-sprayed cylinder bores involving plasma transferred liner material. However, unlike parent metal cylinder bores and press-in cylinder bore liners, thermal-sprayed cylinder bores are more susceptible to cracking and delamination causing engine failure.

While the current engine block and cylinder bore design achieves the initial purpose, the design is susceptible to a specific type of failure in service which can result in a very costly repair. Accordingly, there is a need in the art for an inspection system to ensure initial reliability and long term robustness while maintaining design, cost, and weight improvements.

SUMMARY

The present invention provides a system for inspecting thermal spray coated cylinder bores of aluminum alloy cylinder blocks. The system includes a failure detection apparatus, a heating apparatus, a cooling apparatus, and a control unit in electronic communication with each of the failure detection apparatus, the heating apparatus, and the cooling apparatus. The control unit includes a memory and a control logic sequence for operating the system.

In another example of the present invention, the failure detection apparatus includes at least one acoustic detection device disposed in contact with the cylinder block proximate a first of the cylinder bores.

In yet another example of the present invention, the failure detection apparatus includes one acoustic detection device for each of the cylinder bores of the cylinder block and the acoustic detection devices are mounted on a first fixture.

In yet another example of the present invention, the heating apparatus includes one induction heating element for each of the cylinder bores of the cylinder block and the induction heating elements are mounted on a second fixture.

In yet another example of the present invention, the heating apparatus further includes a temperature control and the heating apparatus is capable of heating the cylinder bores at a rate of 3° C./s to 50° C./s.

In yet another example of the present invention, the heating apparatus further includes a surface temperature monitor and the surface temperature is controlled to not exceed a critical temperature of about 500° C.

In yet another example of the present invention, the cooling apparatus includes one nozzle for each of the cylinder bores of the cylinder block, the nozzles are mounted on a third fixture, and the cooling apparatus provides a pressurized cooling medium to the nozzles.

In yet another example of the present invention, the cooling apparatus further includes a storage tank and the cooling medium is one of compressed air, water, oil, gasses, and mixtures thereof.

In yet another example of the present invention, the cooling apparatus is capable of cooling the cylinder bores of the cylinder block at a rate of between 10° C./s and 100° C./s.

The above features and advantages and other features and advantages of the present invention are readily apparent from the following detailed description of the best modes for carrying out the invention when taken in connection with the accompanying drawings.

BRIEF DESCRIPTION OF THE DRAWING

FIG. 6 is a flowchart depicting a method of operating a cylinder block cylinder bore inspection system in accordance with the present invention.

DESCRIPTION

The following description is merely exemplary in nature and is not intended to limit the present disclosure, application, or uses.

Figure 1:
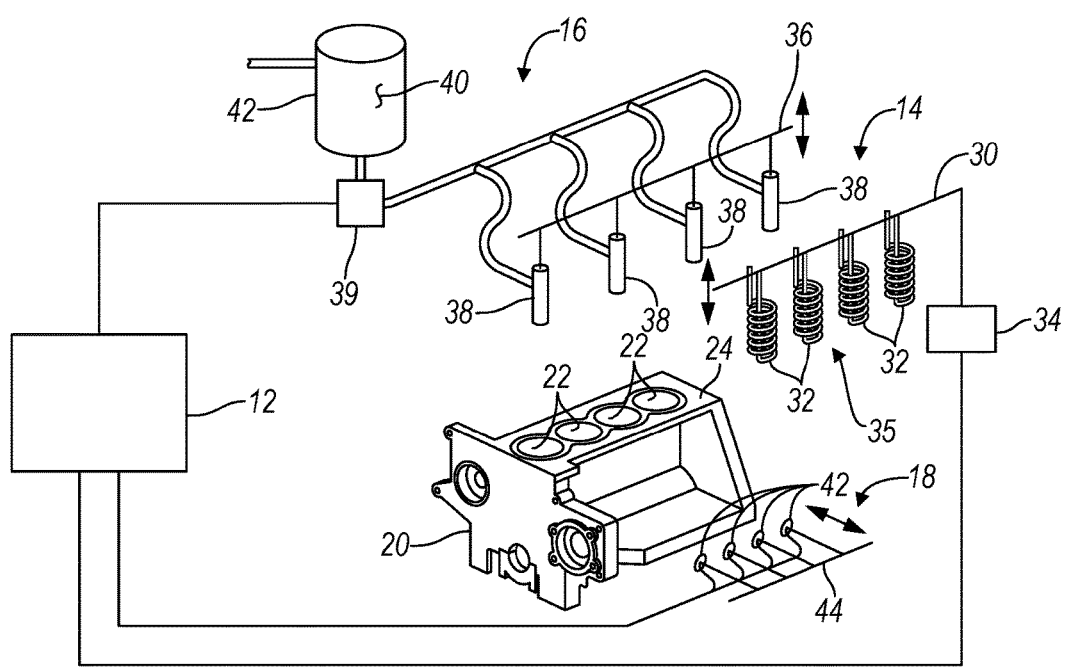
FIG. 1 is a schematic of a cylinder block cylinder bore inspection system in accordance with the present invention.

With initial reference to FIG. 1, a cylinder block cylinder bore inspection system 10 is illustrated and will now be described. The cylinder block cylinder bore inspection system 10 is utilized as an inspection or gauging operation in a cylinder block manufacturing line. Regardless of precisely where the cylinder bore inspection system 10 is placed in the cylinder block manufacturing process, it is important to perform this inspection early in the process prior to performing too many operations and investing too much time on manufacturing the cylinder block. A cylinder bore that fails the inspection process most likely renders the cylinder block unusable without further off-line repairs.

The cylinder bore inspection system 10 includes a processor or control unit 12, a heating apparatus 14, a cooling apparatus 16, and a sensing apparatus 18. A cylinder block 20 is the subject of the inspection. Generally speaking, cylinder blocks 20 are manufactured to provide for engine configurations of multiple shapes and sizes. In-line straight engines may include multiple cylinders with popular designs including engines having four, five, and six cylinders. In the example provided in FIG. 1, the cylinder block 20 includes four cylinder bores 22 aligned in an inline or straight formation such that each axis of the cylinder bores 22 are parallel to each other. Other configurations include 60° or 90° V-engine layouts having from 6 to 12 or even more cylinders. Still other configurations include flat or W layouts having a plurality of cylinders. Thus, the cylinder bore inspection system 10 can be configured to inspect any engine design layout regardless of the number of cylinders or arrangement without departing from the scope of the invention. A top end of each cylinder bore 22 terminates at the head deck 24 while the bottom end of each cylinder bore 22 terminates at the crankcase portion (not shown) of the cylinder block 20.

Figure 2:
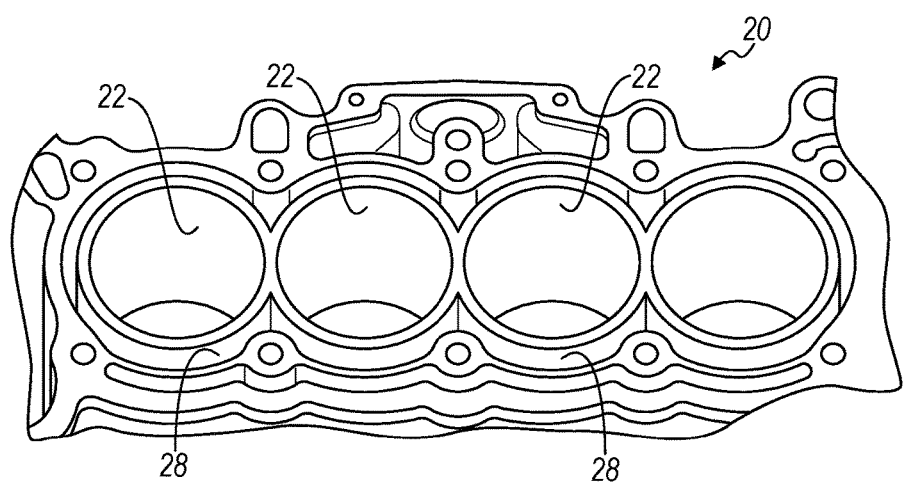
FIG. 2 is a partial perspective view of an aluminum alloy cylinder block having thermal-spray cylinder bores, in accordance with the present invention.

With a quick reference to FIG. 2, the arrangement of the cylinder bores 22 of the cylinder block 20 is explained in more detail. The cylinder bores 22 are arranged in a "Siamese" fashion. More specifically, each cylinder bore 22 shares a bore wall 26 with the adjacent cylinder bore 22. The resulting structure thus provides that a portion of the internal cooling cavities or water jacket 28, does not have any portion of the cooling cavity 28 between the cylinder bores 22. The shared bore wall 26 allows for a more compact design and improves overall stiffness of the structure.

Figure 3:
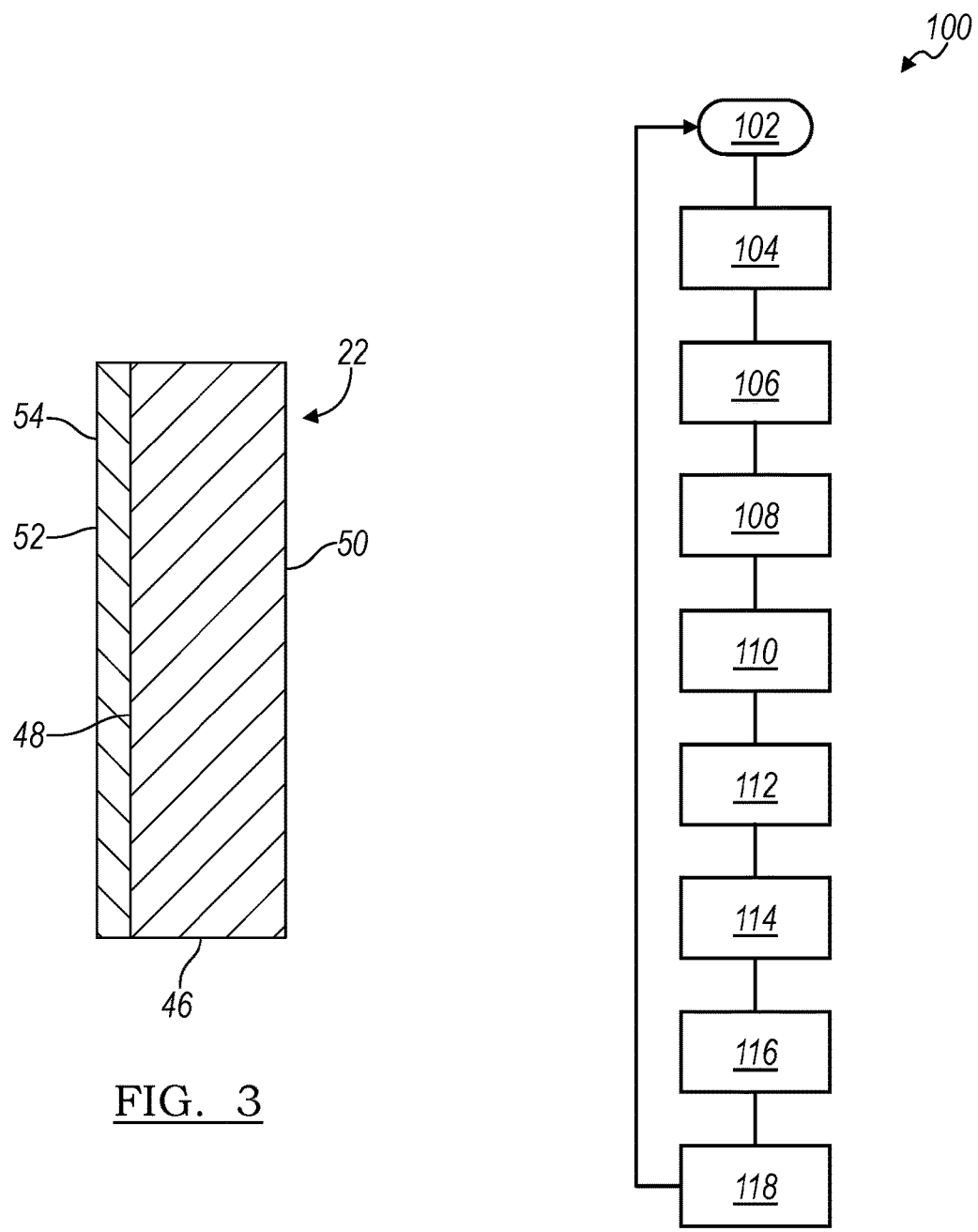
FIG. 3 is a cross sectional view of a cylinder bore wall including a thermal spray coating in accordance with the present invention.

Turning now to FIG. 3 with continuing reference to FIG. 2, a cross section of a wall 46 of the cylinder bore wall 22 after processing through a thermal-spray operation is illustrated and will now be described. The cylinder bore wall 46 includes an inner surface or circumference 48 and an outer surface 50. The outer surface 50 may be adjacent to a cavity utilized as water cooling passages or it may be utilized as a cylinder bore wall 46 of the adjacent cylinder bore 22. In either aspect, the inner surface 48 of the cylinder bore wall 46 is exposed to a reciprocating piston (not shown) when in operation. The inner surface 48 of the cylinder bore wall 46 includes a coating 52 of material that is bonded to a parent material of the cylinder bore wall 46. In some examples, the parent material of the cylinder bore wall 46 may be a cast iron alloy or an aluminum alloy. However, other types of alloys may be used without departing from the scope of the invention. The coating 52 is bonded to the parent material of the cylinder bore wall 46 using any one of a number of methods. One such method is a plasma transferred wire arc thermal spray apparatus as explained in U.S. Pat. No. 5,938,944. Other similar methods or variations of the disclosed methods may be used without departing from the scope of the invention. After the coating 42 is applied to the inner surface 48 of the cylinder bore wall 46, an inner surface 54 of the coating 52 may be machined to achieve a precise fit with the piston and a prescribed surface finish or hone pattern.

Returning now to FIG. 1, the heating apparatus 14 includes a fixture 30, a plurality of induction heating elements 32, and a temperature control mechanism 34. More specifically, the plurality of heating elements 32 include as many individual heating elements as there are cylinder bores 22 in the cylinder block 20. In this example, four individual heating elements 32 are mounted to the fixture 30 so that each of the four heating elements 32 can be inserted into a separate cylinder bore 20 by lowering the fixture 30 or raising the cylinder block 20. The heating elements 32 are induction heating coils 32 capable of heating the cylinder bore 22 at a very rapid rate; from 3° C./s to 50° C./s. The rate of heating can be controlled to tailor the gauge to different cylinder block designs. The heating elements 32 may also include other types of mechanisms, for example, infrared heat lamps, without departing from the scope of the invention. The rapid heat rate creates a large temperature gradient as the surface of the cylinder bore 22 will be at a high temperature before the temperature of the internal material of the cylinder bore 22 starts to increase. Preferably, the surface temperature of the cylinder bore 22 reaches from 200° C. to 500° C. before the heating elements 32 are removed. The heating apparatus also includes a surface temperature monitor 35 for detecting the surface temperature of the cylinder bore 22. The maximum temperature of the surface of the cylinder bore 22 is not to exceed about 500° C. Above this temperature, and the temperature is alloy dependent, the casting microstructure is subject to incipient melting. Thus, the expansion of the metal at the surface of the cylinder bore 22 is restrained by the internal metal of the cylinder bore 22 thus generating thermal stresses in the cylinder bores 22 that approach or exceed thermal stresses produced during operation of the engine in service.

The cooling apparatus 16 is a mechanism for rapidly cooling the material of the cylinder bore 22. The cooling apparatus 16 includes a fixture 36, a plurality of nozzles 38, a cooling medium 40, and a delivery mechanism 39, and depending upon the cooling medium 40 used, a storage tank 42 that is appropriate for that particular cooling medium 40. The cooling apparatus 16 may use water, air, oil, or gases, such as nitrogen and argon, to remove heat from the surface of the cylinder bores 22. In this example, four individual nozzles 38 are mounted to the fixture 36 so that each of the four nozzles 38 can be inserted into a separate cylinder bore 22 by lowering the fixture 36 or raising the cylinder block 20. Once the nozzles 38 are in position, the cooling medium 40 is forced through the nozzles 38 onto the surface of the cylinder bores 22. The target cooling rate for the surface of the cylinder bores 22 is between 10° C./s and 100° C./s. In one example of the present invention, the fixture 36 of the cooling apparatus 16 may be combined with the fixture 30 of the heating apparatus 14 to form a single fixture supporting each of the nozzles 38 of the cooling apparatus 16 and the heating elements 32 of the heating apparatus 14.

The acoustic sensor or transducer apparatus 18 functions to detect audible or vibration signals from the cylinder bores 22 that are produced when the thermal sprayed cylinder bores 22 fail during the thermal cycle testing. The detected failure includes one of the thermal sprayed coating cracking or th thermal sprayed coating delaminating from the substrate or cylinder bore 22 surface. The acoustic sensor apparatus 18 includes at least one acoustical sensor 42 supported by a fixture 44. Prior to the heating apparatus 14 begins the heating process, the fixture 44 of the acoustic sensor apparatus 18 moves the acoustical sensor 42 into a detection position adjacent to the cylinder block 20. In another example, the number of acoustical sensors 42 can match the number of cylinder bores 22 of the cylinder block 20 with each sensor 42 being placed proximate to one cylinder bore 22. In this manner, the acoustic sensor apparatus 18 is capable of identifying which cylinder bore 22 has failed.

The control unit 12 includes data acquisition and data processing capabilities and electronically communicates with the heating apparatus 14, the cooling apparatus 16, and the acoustic sensor or transducer apparatus 18. The processor or control unit 12 generally includes an electronic control device having a preprogrammed digital computer or processor, control logic, memory used to store data, and at least one I/O peripheral. The control logic includes a plurality of logic routines for monitoring, manipulating, and generating data. The control logic may be implemented in hardware, software, or a combination of hardware and software. For example, control logic may be in the form of program code that is stored on the electronic memory storage and executable by the processor or control unit 12.

For example, a control logic or method 100, shown in flowchart form in FIG. 6, is implemented in software program code that is executable by the processor or controller 12 and includes a first control logic 102 for starting the operation after the subject cylinder block is conveyed into position. A second control logic 104 translates the fixture 44 of the acoustic sensor apparatus 18 such that the acoustic sensors 42 are adjacent to or in contact with the corresponding cylinder bores 22 of the cylinder block 20. A third control logic 106 begins the heating of the induction heating elements 32. A fourth control logic 108 translates the fixture 30 of the heating apparatus 14 such that the induction heating elements 32 are inserted into the corresponding cylinder bores 22. After a specified time period, a fifth control logic 110 retracts the fixture 30 of the heating apparatus 14 and translates the fixture 36 of the cooling apparatus 16 such that the nozzles 38 of the cooling apparatus 16 are inserted into the corresponding cylinder bores. A sixth control logic 112 initiates the flow of the cooling medium 40. After a specified period of time, a seventh control logic 114 ends the flow of the cooling medium 40 and retracts the fixture 36 of the cooling apparatus 16. An eighth control logic 116 checks for any failure signals received from the acoustic sensors 42 and reports a test failure or test pass to the operator.

Figure 4:
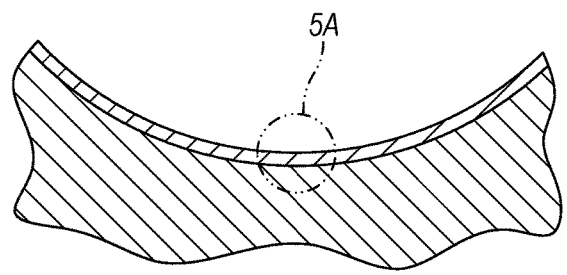
FIGS. 4 and 4A are depictions of a failed thermal-spray cylinder bore in accordance with the present invention.
Figure 4A:
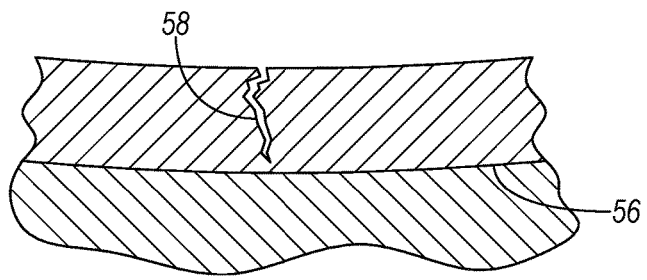
Figure 5:
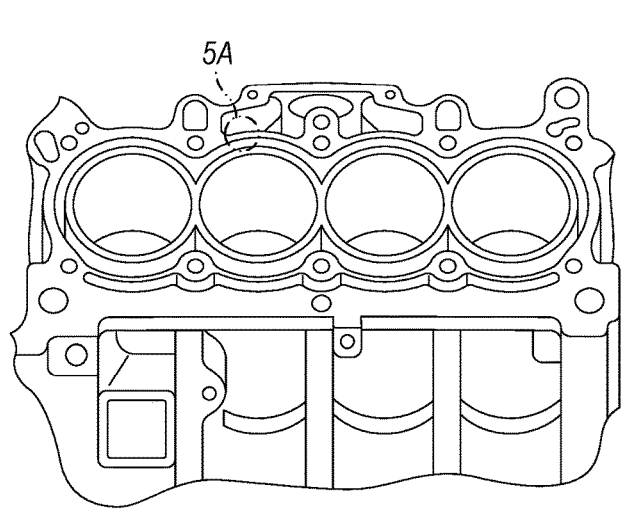
FIGS. 5 and 5A are depictions of a failed thermal-spray cylinder bore in accordance with the present invention.
Figure 5A:
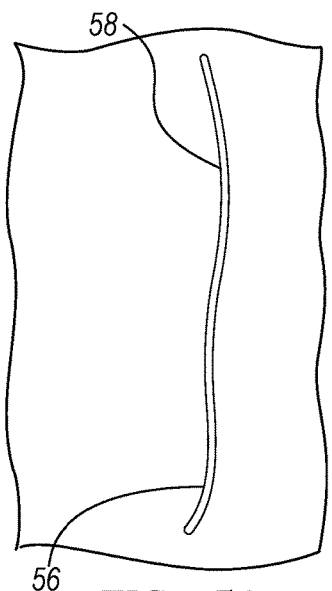

Referring now to FIGS. 4, 4A, 5, and 5A, depictions of failed cylinder bore thermal spray coatings are illustrated and will now be described. For example, FIG. 4 shows micrographs at 6000 μm and 200 μm scale of thermal spray coating delamination 56 and cracking 58 resulting from a failed engine test. In another instance, FIG. 5 depicts an eight cylinder V configuration engine that failed engine testing due to delamination 56 and cracking 58.

While the best modes for carrying out the invention have been described in detail, those familiar with the art to which this invention relates will recognize various alternative designs and examples for practicing the invention within the scope of the appended claims.

The following is claimed:

1. A system for inspecting thermal spray coated cylinder bores of aluminum alloy cylinder blocks, the system including:
   a failure detection apparatus including at least one acoustic detection device disposed in contact with the cylinder block proximate at least one of the cylinder bores;
   a heating apparatus;
   a cooling apparatus, and
   a control unit in electronic communication with each of the failure detection apparatus, the heating apparatus, and the cooling apparatus, and wherein the control unit includes a memory and a control logic sequence for operating the system.

2. The system of claim 1 wherein the failure detection apparatus includes an acoustic detection device for each of the cylinder bores of the cylinder block and the acoustic detection devices are mounted on a first fixture.

3. The system of claim 1 wherein the heating apparatus includes an induction heating element for each of the cylinder bores of the cylinder block and the induction heating elements are mounted on a second fixture.

4. The system of claim 3 wherein the heating apparatus further includes a temperature control and the heating apparatus is capable of heating the cylinder bores at a rate of 3° C./s to 20° C./s.

5. The system of claim 4 wherein the heating apparatus further includes a surface temperature monitor and the surface temperature is controlled to not exceed a critical temperature of about 500° C.

6. The system of claim 1 wherein the cooling apparatus includes a nozzle for each of the cylinder bores of the cylinder block, the nozzles are mounted on a third fixture, and the cooling apparatus provides a pressurized cooling medium to the nozzles.

7. The system of claim 6 wherein the cooling apparatus further includes a storage tank and the cooling medium is one of compressed air, water, oil, and gases.

8. The system of claim 7 wherein the cooling apparatus is capable of cooling the cylinder bores of the cylinder block at a rate of between 10° C./s and 100° C./s.

9. A system for inspecting thermal spray coated cylinder bores of aluminum alloy cylinder blocks, the system including:
   a failure detection apparatus having at least one acoustic detection device disposed adjacent with the cylinder block proximate a first of the cylinder bores;
   a heating apparatus having one induction heating element for each of the cylinder bores of the cylinder block and the induction heating elements are mounted on a first fixture;
   a cooling apparatus having a nozzle for each of the cylinder bores of the cylinder block, and wherein the nozzles are mounted on a second fixture and the cooling apparatus provides a pressurized cooling medium to the nozzles, and
   a control unit in electronic communication with each of the failure detection apparatus, the heating apparatus, and the cooling apparatus, and wherein the control unit includes a memory and a control logic sequence for operating the system.

10. The system of claim 9 wherein the failure detection apparatus includes an acoustic detection device for each of the cylinder bores of the cylinder block and the acoustic detection devices are mounted on a second fixture.

11. The system of claim 10 wherein the heating apparatus further includes a temperature control and the heating apparatus is capable of heating the cylinder bores at a rate of 3° C./s to 20° C./s.

12. The system of claim 11 wherein the cooling apparatus further includes a storage tank and the cooling medium is one of compressed air, water, oil, and gases.

13. The system of claim 12 wherein the cooling apparatus is capable of cooling the cylinder bores of the cylinder block at a rate of between 10° C./s and 100° C./s.

14. The system of claim 12 wherein the control logic sequence includes:
   a first control logic for translating the second fixture of the failure detection apparatus such that the acoustic sensors are adjacent to the corresponding cylinder bores of the cylinder block;
   a second control logic for initiating heating of the induction heating elements;
   a third control logic for translating the first fixture of the heating apparatus such that the induction heating elements are inserted into the corresponding cylinder bores;
   a fourth control logic for retracting the first fixture of the heating apparatus after a specified time period and translating the third fixture of the cooling apparatus such that the nozzles of the cooling apparatus are inserted into the corresponding cylinder bores;

a fifth control logic for initiating the flow of the cooling medium;

a sixth control logic for ending the flow of the cooling medium after a specified time period and retracting the third fixture of the cooling apparatus; and a seventh control logic for checking for any failure signals received from the acoustic sensors and reporting a test failure or test pass to the operator.

15. A system for inspecting thermal spray coated cylinder bores of aluminum alloy cylinder blocks, the system including:

a failure detection apparatus;

a heating apparatus;

a cooling apparatus, and a control unit in electronic communication with each of the failure detection apparatus, the heating apparatus, and the cooling apparatus, and wherein the control unit includes a memory and a control logic sequence for operating the system and the control logic sequence includes:

a first control logic for translating the failure detection apparatus such that the failure detection apparatus is adjacent to the cylinder bores of the cylinder block;

a second control logic for initiating heating of the heating apparatus;

a third control logic for translating the heating apparatus such that the heating apparatus is inserted into the cylinder bores of the cylinder block;

a fourth control logic for retracting the heating apparatus after a specified time period and translating the cooling apparatus such that the cooling apparatus is inserted into the cylinder bores of the cylinder block;

a fifth control logic for initiating the flow of a cooling medium through the cooling apparatus;

a sixth control logic for ending the flow of the cooling medium after a specified time period and retracting the cooling apparatus; and a seventh control logic for checking for any failure signals received from the failure detection apparatus and reporting a test failure or test pass to the operator.

16. The system of claim 15 wherein the failure detection apparatus includes an acoustic detection device for each of the cylinder bores of the cylinder block and the acoustic detection devices are mounted on a first fixture.

17. The system of claim 15 wherein the heating apparatus includes a temperature controller and an induction heating element for each of the cylinder bores of the cylinder block, and wherein the heating apparatus is capable of heating the cylinder bores at a rate of 3° C./s to 20° C./s.

18. The system of claim 15 wherein the cooling apparatus includes a storage tank and a nozzle for each of the cylinder bores of the cylinder block, and wherein the nozzles are mounted on a third fixture and the cooling apparatus provides a pressurized cooling medium to the nozzles.

19. The system of claim 18 wherein the cooling apparatus is capable of cooling the cylinder bores of the cylinder block at a rate of between 10° C./s and 100° C./s.

* * * * *